United States Patent [19]
Krane et al.

[11] Patent Number: 5,972,623
[45] Date of Patent: Oct. 26, 1999

[54] COLLAGEN-PEPTIDE ASSAY METHOD

[75] Inventors: Stephen M. Krane, Waban; Michael H. Byrne, Town of Dracut, both of Mass.; Hsin-Shan Julia Ju, Cupertino; Scott D. Leigh, Castro Valley, both of Calif.

[73] Assignee: Metra Biosystems, Inc., Mountain View, Calif.

[21] Appl. No.: 09/127,286

[22] Filed: Jul. 31, 1998

Related U.S. Application Data

[60] Provisional application No. 60/054,369, Jul. 31, 1997.

[51] Int. Cl.$^6$ ................................................ G01N 33/53
[52] U.S. Cl. ...................... 435/7.1; 435/326; 435/331; 435/346; 435/975; 436/518; 530/327; 530/328; 530/356; 530/387.9; 530/388.1; 530/391.1
[58] Field of Search .......................... 435/7.1, 326, 331, 435/346, 975; 436/518; 530/327, 328, 356, 387.9, 388.1, 391.1

[56] References Cited

U.S. PATENT DOCUMENTS

| | | |
|---|---|---|
| 4,628,027 | 12/1986 | Gay . |
| 5,538,853 | 7/1996 | Risteli et al. . |
| 5,731,409 | 3/1998 | Fields et al. . |
| 5,750,647 | 5/1998 | Eyre et al. ............................... 530/328 |

FOREIGN PATENT DOCUMENTS

| | | |
|---|---|---|
| 401 370 A1 | 12/1990 | European Pat. Off. . |
| 505 210 A2 | 9/1992 | European Pat. Off. . |
| 505 210 A3 | 9/1992 | European Pat. Off. . |
| 304 292 B1 | 2/1994 | European Pat. Off. . |
| 465 104 B1 | 9/1996 | European Pat. Off. . |
| 829 724 A1 | 3/1998 | European Pat. Off. . |
| WO 89/04491 | 5/1989 | WIPO . |
| WO 89/12824 | 12/1989 | WIPO . |
| WO 91/08478 | 6/1991 | WIPO . |
| WO 91/10141 | 7/1991 | WIPO . |
| WO 92/21698 | 12/1992 | WIPO . |
| WO 94/03814 | 2/1994 | WIPO . |
| WO 94/14072 | 6/1994 | WIPO . |
| WO 94/15844 | 7/1994 | WIPO . |
| WO 95/08115 | 3/1995 | WIPO . |
| WO 96/12193 | 4/1996 | WIPO . |
| WO 96/30765 | 10/1996 | WIPO . |

OTHER PUBLICATIONS

International Search Report based on PCT Application No. US98/16224.

Chu, Mon–Li, et al., "Human proα1(I) collagen gene structure reveals evolutionary conservation of a pattern of introns and exons," Nature 310: 337–340 (1984).

Eyre, David R., "Cross–Linking in Collagen and Elastin," Ann Rev Biochem 53:717–48 (1984).

Eyre, David, "Collagen Cross–Linking Amino Acids," Methods in Enzymology 144: 115–138 (1987).

Ju, J. et al., "A New Marker for Measuring Bone Resorption Using an ELISA for a 14 amino Acid Peptide (Residues 620–633) Derived form the Collagen α1 (I) Chain,"J. Bone and Mineral Res. vol. 12 No. Suppl. Aug. 1997, p. 307.

Kivirikko, K. I., "Urinary Excretion of Hydroxyproline in Health and Disease," *International Review of Connective Tissue Research vol. 5*, David A Hall and D.S. Jackson (ed.), Academic Press, N.Y., 1970, pp. 93–162.

Krane, S.M, et al., "Urinary Polypeptides Related to Collagen Synthesis," The Journal of Clinical Investigation 49: 716–729 (1970).

Krane, S.M., et al., "Collagen–Like Fragments: Excretion in Urine of Patients with Paget's Disease of Bone," Science 157: 713–716 (1967).

Macek, J. et al., "Determination of collagen degradation products in human urine in osteoarthritis," Z. Rheumatol 46:237–240 (1987).

Simon, L.S., et al., "Serum Levels of Type I and TypeII Procollagen Fragments in Paget's Disease of Bone," J. of Clinical Endocrinology and Metabolism, 56(1): 110–120 (1984).

Tellerova, K. et al., "Determination of Larger Urinary Peptides in Osteoarthrosis by High–Performance Liquid Chromatography," Scand J Rheumatology 15:52–56 (1986).

Timpl, R., et al., "Antibodies of Distinct Types of Collagens and Procollagens and Their Application in Immunohistology," J. of Immunological Methods 18: 165–182 (1977).

Werkmeister, et al., "Characterization of a monoclonal antibody against native human type I collagen," J. Biochem 187:439–443 (1990).

*Primary Examiner*—Jeffrey Stucker
*Attorney, Agent, or Firm*—Vincent M. Powers; Dehlinger & Associates

[57] ABSTRACT

The invention includes a method of determining the level of Type I collagen fragments in a biological fluid using an antibody which is immunospecific for an epitope contained in one of the following sequences:

(1) Ala-Hyp-Gly-Asp-Arg-Gly-Glu-Hyp-Gly-Pro-Hyp-Gly-Pro-Ala, or (2) Gly-Asn-Ser-Gly-Glu-Hyp-Gly-Ala-Hyp.

under conditions effective to allow determination of the level of collagen fragments in the sample which contain the epitope. The method is useful for assessing the level of bone collagen degradation, particularly in humans. Also disclosed are antibodies and kits which can be used in the method.

20 Claims, 5 Drawing Sheets

SEQUENCE LISTING

```
<160> NUMBER OF SEQ ID NOS: 4

<210> SEQ ID NO 1
<211> LENGTH: 14
<212> TYPE: PRT
<213> ORGANISM: H. sapiens
<220> FEATURE:
<221> NAME/KEY: PEPTIDE
<222> LOCATION: (1)...(14)
<223> OTHER INFORMATION: peptide isolated in human urine
<220> FEATURE:
<221> NAME/KEY: MOD_RES
<222> LOCATION: (2)...(2)
<223> OTHER INFORMATION: 4Hyp
<220> FEATURE:
<221> NAME/KEY: MOD_RES
<222> LOCATION: (8)...(8)
<223> OTHER INFORMATION: 4Hyp
<220> FEATURE:
<221> NAME/KEY: MOD_RES
<222> LOCATION: (11)...(11)
<223> OTHER INFORMATION: 4Hyp

<400> SEQUENCE: 1
```

Ala Xaa Gly Asp Arg Gly Glu Xaa Gly Pro Xaa Gly Pro Ala
 1               5                  10

<210> SEQ ID NO 2
<211> LENGTH: 9
<212> TYPE: PRT
<213> ORGANISM: H. sapiens
<220> FEATURE:
<221> NAME/KEY: PEPTIDE
<222> LOCATION: (1)...(9)
<223> OTHER INFORMATION: peptide isolated from human urine
<220> FEATURE:
<221> NAME/KEY: MOD_RES
<222> LOCATION: (6)...(6)
<223> OTHER INFORMATION: 4Hyp
<220> FEATURE:
<221> NAME/KEY: MOD_RES
<222> LOCATION: (9)...(9)
<223> OTHER INFORMATION: 4Hyp

<400> SEQUENCE: 2

Gly Asn Ser Gly Glu Xaa Gly Ala Xaa
 1               5

<210> SEQ ID NO 3
<211> LENGTH: 15
<212> TYPE: PRT
<213> ORGANISM: Artificial Sequence
<220> FEATURE:
<223> OTHER INFORMATION: artificial peptide sequence corresponding to
      SEQ ID NO:1, to which a Cys residue has been added to
      N-terminus
<220> FEATURE:
<221> NAME/KEY: MOD_RES
<222> LOCATION: (3)...(3)
<223> OTHER INFORMATION: 4Hyp
<220> FEATURE:
<221> NAME/KEY: MOD_RES
<222> LOCATION: (9)...(9)
<223> OTHER INFORMATION: 4Hyp
<220> FEATURE:
<221> NAME/KEY: MOD_RES
<222> LOCATION: (12)...(12)
<223> OTHER INFORMATION: 4Hyp

<400> SEQUENCE: 3

Cys Ala Xaa Gly Asp Arg Gly Glu Xaa Gly Pro Xaa Gly Pro Ala
 1               5                  10                  15

<210> SEQ ID NO 4
<211> LENGTH: 10
<212> TYPE: PRT
<213> ORGANISM: Artificial Sequence
<220> FEATURE:
<221> NAME/KEY: PEPTIDE
<222> LOCATION: (1)...(10)
<223> OTHER INFORMATION: artificial peptide sequence corresponding to
      SEQ ID NO: 2, to which a Cys residue has been added to
      the N-terminus
<220> FEATURE:
<221> NAME/KEY: MOD_RES
<222> LOCATION: (7)...(7)
<223> OTHER INFORMATION: 4Hyp
<220> FEATURE:
<221> NAME/KEY: MOD_RES
<222> LOCATION: (10)...(10)
<223> OTHER INFORMATION: 4Hyp

<400> SEQUENCE: 4

Cys Gly Asn Ser Gly Glu Xaa Gly Ala Xaa
 1               5                  10

COLLAGEN-PEPTIDE ASSAY METHOD

This application claims priority under 35 U.S.C. §120 to U.S. Provisional Application Ser. No. 60/054,369 filed Jul. 31, 1997, which is incorporated herein by reference.

FIELD OF THE INVENTION

The present invention relates to a method for assessing certain collagen fragments in biological fluids. In one embodiment, the invention relates to a method of evaluating the level of collagen degradation in mammalian subjects, particularly humans, and to the diagnosis and monitoring of medical conditions associated with abnormal collagen metabolism.

REFERENCES

Alberts, B., et al., MOLECULAR BIOLOGY OF THE CELL, 2ND ED., Garland Publishing, Inc., New York, N.Y., pp. 808–815 (1989).
Baylink, PCT Publication WO 94/14844 (1994).
Bergman, R., et al., *Anal. Chem* 35:1961 (1963).
Campbell, A., *MONOCLONAL ANTIBODY AND IMMUNOSENSOR TECHNOLOGY,* Elsevier (1991).
Cerelli, M. J., et al., PCT Publication WO 94/03814 (1994).
Eyre, D., METH. ENZYMOL. 144:117 (1987).
Eyre, D., PCT Publication WO 89/04491 (1989).
Gosling, J., *Clin. Chem.* 36:1408 (1990).
Harlow, E., et al., ANTIBODIES: A LABORATORY MANUAL, Cold Spring Harbor Lab, Cold Spring Harbor, N.Y. (1988).
Krane, S. M., et al., *Science* 157:713 (1967).
Krane, S. M., et al., *J. Clin Invest.* 49:716 (1970)
Kung, V. T., et al., PCT Publication WO 94/14072 (1994).
Miller, E., and Rhodes, R., "Preparation and Characterization of Invertebrate Collagens" in *Methods Enzymol.* 82:Part A, pp. 33–64 (1982).
Risteli, J., EP Patent Pub. 505210 A2 (1992).
Robins, S. P., PCT Publication WO 91/10141 (1991).
Segel, I., *BIOCHEMICAL CALCULATIONS,* John Wiley and Sons, Media, Pa. (1976).
Taylor, A. K., et al., OSTEOPOROSIS 20:589 (1994)
van der Rest, M., et al., EUR. J. BIOCHEM. 125:491 (1982).
Wong, S. S., CHEMISTRY OF PROTEIN CONJUGATION AND CROSSLINKING, CRC Press, Boca Raton, Fla. (1991).

BACKGROUND OF THE INVENTION

There are numerous disease states in humans which are characterized by a high level of bone resorption and/or an abnormal balance between bone formation and bone resorption. Among the more common of these are osteoporosis, osteoarthritis, rheumatoid arthritis, and conditions related to the progress of benign and malignant tumors of the bone and metastatic cancers that have migrated to bone cells from elsewhere in the body, e.g., from prostate or breast initial tumors. Other conditions associated with changes in collagen metabolism include osteomalacial diseases, rickets, abnormal growth in children, renal osteodystrophy, and drug-induced osteopenia. Further, abnormalities in bone metabolism are often side effects of thyroid treatment and thyroid conditions per se, such as primary hyperparathyroidism and thyrotoxicosis as well as Cushing's disease.

The organic matrix of bone consists of approximately 90% of type I collagen, which contains two α1 and one α2 chain coiled around each other to form a triple helix. The helical domain of each chain is preceded by a short N-telopeptide and is followed by a short C-telopeptide. The biosynthetic pathways leading to formation and maturation of Type I collagen have been described (e.g., Alberts et al., 1989; Eyre, 1987). Collagen chains are initially synthesized as procollagen chains which associate to form trimeric, triple helical complexes. Following secretion into the extracellular space, the trimeric molecules are cleaved to release the propeptides from the N- and C-termini to form collagen (also known as tropocollagen) molecules. The collagen molecules associate to form rod-shaped fibrils in which the molecules are packed in parallel, staggered arrays. Formation of various intra- and intermolecular crosslinks within and between adjacent collagen molecules impart increased stability.

In mammals, the formation and maintenance of bone collagen tissues is understood to be a dynamic process mediated by bone forming cells (osteoblasts) and bone degrading cells (osteoclasts). An imbalance between the rates of bone formation and bone degradation, and particularly elevation in bone degradation, can result in serious pathological conditions deleterious to health.

Over the past several decades, various methods for diagnosing or monitoring abnormalities of bone collagen degradation have been proposed. For example, hydroxyproline, a major constituent of collagen polypeptides, was proposed as a possible marker in urine many years ago. There are, however, several disadvantages with the use of measurement of hydroxyproline as a marker, including the need for a lengthy acid-hydrolysis step, a lack of specificity for Type I collagen (from bone), and the substantial metabolism of free hydroxyproline in the liver. In summary, hydroxyproline has been rejected as a clinical marker for bone resorption conditions.

Hydroxylysine and certain glycosylated forms thereof have been proposed, but use of these markers has been limited due to the lack of a convenient assay method suitable for general clinical use, as well as by the need for an acid hydrolysis pretreatment step, like hydroxyproline.

Certain terminal fragments of collagen have also been investigated for possible diagnostic applications. Prior to the applicants' present invention, it was generally believed in the art that peptides originating from the helical regions of collagen could not be used as indicators of bone resorption because of substantial degradation caused by endogenous proteases in the extracellular space, blood circulation, and urine. Accordingly, practitioners in the art have focused on measuring fragments from the telopeptide regions of collagen that contain crosslinking species such as pyridinoline crosslinks, which presumably protect associate collagen chain regions from proteolytic degradation (e.g., Risteli, 1992). Methods for measuring such telopeptide fragments have been described, for example, in WO 89/04491 (Eyre), WO 95/08115 (Qvist), and WO 94/14844 (Baylink). Methods have also been described for measuring telopeptide crosslinks themselves, without attached collagen chains (see Robins, WO 91/10141; Cerelli et al., WO 94/03814; and Kung et al., WO 94/14072).

Telopeptide fragments have been reported to be useful in connection with bone resorption conditions. However, procollagen peptide species have been reported to be useful for measuring of bone formation (e.g., Taylor, 1994), a process that is irrelevant to most bone resorption-related diseases.

Accordingly, there remains a need to develop new markers which are useful for diagnosing and monitoring abnormal bone resorption conditions. Ideally, such a marker should be measurable in biological fluids such as urine and serum, conveniently by immunoassay. The marker should be useful in diagnosing the presence of bone resorption disorders which are characterized by above-normal levels of bone degradation. In addition, the marker should be useful for detecting changes in the status of bone degradation in the subject over time, particularly in response to therapeutic treatment.

SUMMARY OF THE INVENTION

The present invention is based in part on the applicants' discovery of an immunoassay method for measuring peptide fragments that contain certain regions from the helical domain of the α1(I)chains of Type I collagen in a body fluid, which is particularly useful for determining or monitoring the level of bone collagen degradation in a mammalian subject.

The present invention includes, in one aspect, a method for determining the level of Type I collagen fragments in a fluid sample. In the method, the fluid sample is contacted with an antibody which is immunospecific for an epitope contained in one the following peptide sequences:
(1) Ala-Hyp-Gly-Asp-Arg-Gly-Glu-Hyp-Gly-Pro-Hyp-Gly-Pro-Ala (SEQ ID NO:1) or
(2) Gly-Asn-Ser-Gly-Glu-Hyp-Gly-Ala-Hyp (SEQ ID NO:2)
under conditions effective to form a complex between the antibody and polypeptide fragments containing said epitope in the sample. The level of complex formed is determined, and from this, the level of polypeptide fragments that contain the epitope is determined. The antibody used in the method can be polyclonal or monoclonal, and preferably is monoclonal. The sample that is tested is preferably urine or blood, although other fluid samples are also contemplated.

In a preferred embodiment, the method of the invention can be used to assess the level of bone collagen degradation in a mammalian subject, particularly in humans. Thus, the invention includes a method for determining the level of bone collagen degradation in a mammalian subject. In the method, a body fluid sample from the subject is contacted with an antibody which is immunospecific for an epitope contained in one the polypeptide sequences noted above, under conditions effective to form a complex between the antibody and polypeptide fragments containing the epitope in the sample. From the level of complex formed, the level of polypeptide fragments that contain the epitope in the sample is determined. A measured fragment level that is elevated relative to a normal level is an indication that the subject has a bone resorption disorder.

The method is useful in screening for the presence of bone disorders characterized by an elevated level of bone collagen resorption. In one set of embodiments, the method may be used to screen for the presence of a bone disorder selected from any one or more of the group consisting of osteoporosis, osteoarthritis, hyperparathyroidism, rheumatoid arthritis, Paget's disease, or a metastatic bone cancer condition.

In another general embodiment, the method can be used to monitor bone resorption over time, particularly in response to a therapeutic treatment.

In another aspect, the invention includes an antibody which is immunoreactive with one of the antigenic peptides defined above.

The invention also includes a kit for measuring the level of Type I collagen fragments in a fluid sample. The kit includes an antibody of the type described above, and preferably also includes an immunogenic standard containing the peptide for which the antibody is immunospecific. Typically, the kit includes instructions and other reagents necessary for successful conduct of the assay.

Preferably, the means of detection used in the method or kit includes a reporter enzyme which is effective to produce a calorimetric signal, although other formats can be used.

In one general embodiment, the kit includes a solid-phase support to which the antibodies are bound for capturing the collagen fragments to be detected in the sample. In a second embodiment, a peptide or polypeptide containing the epitope to be detected is bound directly or indirectly to a solid-phase support, for competing with the collagen fragments to be detected in the sample.

Also forming part of the invention is a method for producing monoclonal antibodies which are useful in the method and kit above. The method includes forming a hybridoma composed of the fusion product of (a) spleen cells from an animal immunized with a selected epitope-containing peptide as defined above, preferably attached to a carrier substance, and (b) an immortalizing fusion partner, and selecting hybridomas that are immunospecific with the selected epitope.

The invention also includes a method for producing polyclonal antibodies that are useful in the method and kit above. The method includes immunizing an animal with an immunogen as described herein, collecting an antiserum that is produced as a result of the immunization, and selecting for antibodies that have an average binding affinity of at least $10^7$/molar for an epitope as described herein.

The invention also includes an immunogen for use in preparing an antibody reagent such as described above. The immunogen consists essentially of one of the peptide sequences noted above, or a shorter sequence therein, coupled to a suitable carrier. One preferred carrier is keyhole limpet hemocyanin.

In another embodiment, the invention includes a method of assessing the effect of a selected substance, such as a drug, on the level of expression or secretion of type I collagen and/or fragments thereof by a cell or tissue preparation. In the method, a selected cell or tissue is exposed to the substance, after which a culture fluid supernatant or extract of the cell or tissue is contacted with an antibody specific for an epitope as described above, under conditions effective to form a complex between the antibody and any polypeptide fragments containing the epitope in the sample. From the amount of complex formed, the level of polypeptides that contain the epitope is determined, such that an increase in the measured level relative to the level observed in the absence of exposure to the substance indicates that the substance enhances production of such polypeptides, and a decrease indicates that the substance reduces production of such polypeptides. The method is useful, for example, for identifying and/or characterizing substances that reduce osteoclastic (resorptive) activities in collagen-containing cells and tissues.

In another embodiment, the invention includes a method of assessing the effect of a selected substance, such as a drug, on helicopeptide levels in a body fluid of an animal model such as rats, mice, cats, dogs, monkeys, etc, using an immunoassay method as described above. The method is useful, for example, for identifying and/or characterizing substances and therapies that reduce the level of bone resorption.

These and other objects and features of the invention will become more fully apparent when the following detailed description of the invention is read in conjunction with the accompanying drawings.

DETAILED DESCRIPTION OF THE INVENTION

I. Definitions

Figure 1:
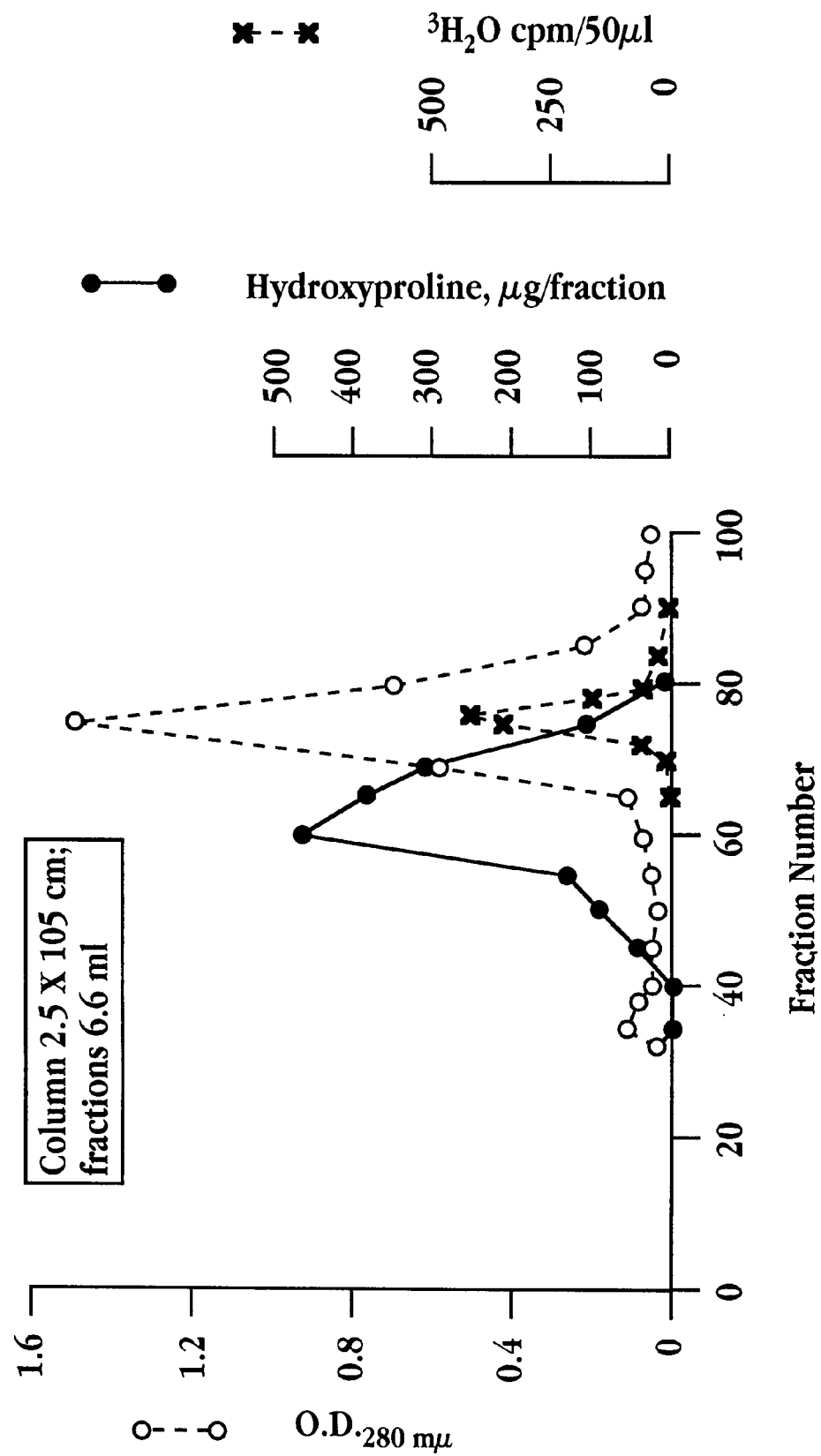
FIG. 1 shows an initial chromatographic separation of hydroxyproline (Hyp)-containing fractions from the urine of patients with Paget's disease.

The terms and phrases below have the following meanings unless indicated otherwise.

"Blood sample" is intended to encompass blood in any form suitable for analysis, such as serum or plasma prepared by standard methods.

"Biological fluid" as used herein encompasses any biological fluid that is commonly tested in clinical samples, including body fluids such as blood, urine, saliva, and sweat, as well as extracts and supernatants of cells and/or tissues.

"Polypeptide" means a polymer of at least two contiguous amino acid residues and containing at least one peptide bond.

"Peptide" means a polypeptide of 50 or fewer contiguous amino acid residues.

The term "antibody" includes monoclonal and polyclonal antibodies, as well as fragments thereof. When used in the context of a method of measuring or determining collagen fragments, "antibody" is generally intended to encompass any analyte-specific binding partner, however it is produced.

The term "epitope" refers to the minimum amino acid sequence in a polypeptide that is recognized by, and thus determines the immunospecificity of, an antibody which binds such an epitope in a polypeptide. In the context of the present invention, an epitope can be as short as three contiguous amino acid residues, and more typically includes four or more contiguous residues. The actual length of the epitope for which an antibody is specific can be determined empirically by conducting binding studies with peptides containing various candidate epitopes bordered by non-epitopic residues.

"Mammal" is intended to have its standard meaning, including, for example, mice, rabbits, sheep, dogs, cats, horses, and humans.

II. Preparation of Antibodies

A. Immunogen

The immunogen used to produce an antibody of the invention preferably includes a peptide sequence corresponding to SEQ ID NO:1 or SEQ ID NO:2 as identified above, or a shorter sequence selected therefrom, which may be coupled covalently to a suitable carrier. Typically, the immunogen will contain an epitope comprising at least three contiguous residues from SEQ ID NO:1 or SEQ ID NO:2. Such peptides may be prepared by conventional chemical or recombinant methods, or from natural sources, by methods known in the art or described herein.

Fragments containing the above-identified sequences were isolated and sequenced by the applicants from human urine, as described in Example 1. The amino acid sequence of the first peptide, designated SEQ ID NO:1, corresponds to residues 620–633 of the collagen α1(I)chain, and is referred to herein as "helicopeptide I" or "helicopeptide/α1(I)$^{620-633}$". The amino acid sequence of the second peptide, SEQ ID NO:2, corresponds to residues 253–261 of the collagen α1(I)chain and is referred to herein as "helicopeptide I'" or "helicopeptide/α1(I)$^{253-261}$". Synthetic peptides having these sequences were prepared as described in Example 2.

In addition to containing the epitope of interest, an epitope-containing peptide for use as immunogen may include additional residues or attached moieties which serve to link the peptide to the carrier. In a preferred approach, a cysteine residue is incorporated into the peptide at its N- or C-terminus to facilitate covalent attachment to the carrier, as illustrated in Example 2.

The carrier for the immunogen may be any protein, such as bovine serum albumin (BSA) or keyhole limpet hemocyanin (KLH), which has low immunogenicity by itself and which, when attached to a peptide of interest, facilitates an immunological response against the peptide. Alternatively, one or more of the selected peptide of interest may be attached to a molecular scaffold, such as a polyamine, which is suitable for presenting the peptide to an animal's immune system. A variety of suitable carrier molecules are known in the art.

Coupling of the peptide immunogen to the carrier molecule is by standard coupling methods, typically using a bifunctional coupling agent whose reactive groups are reactive towards functional groups on the carrier and peptide, respectively. For example, for coupling a cysteine-containing peptide to the amino groups of KLH, SPDP (N-succinimidyl 3-(2-pyridyldithio)propionate, or sulfo-SMCC (sulfo-N-succinimidyl 4-(N-maleimidomethyl) cyclohexane-1-carboxylate) (Wong, 1991) may be used. This reagent contains an activated ester group which can react with amino groups of KLH to form amide linkages, and an activated disulfide which can react with a cysteine thiol group of the peptide immunogen to form a new disulfide. An illustrative method for attaching a carrier protein to peptide antigens is provided in Example 3A.

Alternatively, the peptide immunogen can be coupled directly to the carrier, e.g., in the presence of a water-soluble carboxyl activating agent such as EDC (1-(3-dimethylaminopropyl)-3-ethylcarbodiimide), also according to standard methods. General coupling reactions for derivatizing a carrier protein with a peptide antigen are given in Harlow, et al. (1988), pp. 77–87, and in Wong (1991).

B. Monoclonal Antibodies

To prepare a monoclonal antibody reagent in accordance with the invention, an immunogen such as described above is used to immunize an animal, such as a mouse, from which antigen-specific lymphocytes can be obtained for immortalization. A number of suitable mouse lines have been developed for this purpose, including the well known Balb/c mouse as well as mouse lines having heightened immune responses, such as the "autoimmune" MRL/MpJ-lpr mouse available from Jackson Laboratory (Bar Harbor, Minn.).

The selected animal is typically immunized using a series of injections of immunogen in accordance with protocols known in the art. For example, each immunization may be carried out intraperitoneally with aliquots of immunogen (e.g., 100 µg) in a suitable adjuvant (e.g., Ribi(CWS), available from RIBI Immunochem Research, Inc., Hamilton, Mont.). An exemplary immunization protocol is described in Example 4.

Spleen cells are usually harvested about 8 weeks after initial immunization, and fused with an immortal cell line such as the P3X63Ag8.653 myeloma cell line. Selection for successful fusion products can be performed in HAT in conditioned S-DMEM medium, according to published methods (see, generally, Harlow, et al., pp. 196–212, 1988). One useful supplemented medium is DMEM (Dulbecco's modified Eagle's medium, available from Gibco, N.Y.), supplemented according to the formulation: DMEM (80%), NCTC-109 (10%), fetal clone bovine serum (10%), oxaloacetic acid (1 mM), L-glutamine (2 mM) gentamicin (50 $\mu$g/mL) and insulin (10 $\mu$g/mL).

Conditioned, supplemented DMEM ("conditioned S-DMEM") can be prepared by growth of IL-1-secreting mouse monocyte cell line P388D1, or interchangeably, cell line J774A.1, in S-DMEM, with a 1:4 split twice a week. Every 3 days, tissue culture supernatants are filtered through a 0.2 micron filter and then supplemented with 4 mM L-glutamine. The resultant concentrated, conditioned S-DMEM can then be used as a supplement for un-conditioned S-DMEM (e.g., unconditioned S-DMEM is supplemented 20% (v:v) with P388D1 conditioned medium, or 10% with J774A.1-conditioned medium) to raise hybridoma cells. Spleen cells which serve as feeders can also be added to S-DMEM to support the growth of hybridoma cells.

Successful fusion products are then screened for immunoreactivity with the helicopeptide, typically using a competitive immunoassay format. Cell lines which show high affinity binding to the immunogen are subcloned by limiting dilution and are further screened for production of antibodies with high binding affinity for the epitope of interest.

To produce the antibody reagent, the hybridoma cell line is grown in a suitable medium (Harlow, et al., pp. 247–270, 1988), such as Dulbecco's modified Eagle's medium (DMEM) supplemented as described in the Examples. Monoclonal antibodies ("Mabs") are harvested from the medium and can be concentrated and stored according to published methods (Harlow, et al. pp. 271–318, 1988).

Screening experiments carried out in support of the invention (Example 4) resulted in identification of a high percentage of successful fusion products for KLH-immunogens (3) and (4), where immunogen (3) contains the helicopeptide I sequence from above, and immunogen (4) contains the helicopeptide II sequence. Following the identification of antibody-producing hybridoma clones, a competitive reverse ELISA was employed to select clones exhibiting both high sensitivity and specificity toward helicopeptide. Based on this selection process, clone 10B1, which produces monoclonal antibodies specific for SEQ ID NO:1, was selected for further illustration of the invention.

C. Polyclonal Antibodies

Polyclonal antibody preparation is by conventional techniques, including injection of an immunogen into suitable mammalian subjects, such as rabbits, mice, rats, or sheep according to immunological protocols generally known in the art, e.g., Harlow, et al., pp. 93–115 (1988). Typically, rabbits are injected subcutaneously with the immunogen in an adjuvant, and booster immunizations are given by subcutaneous or intramuscular injection every 2–3 weeks; mice may be injected intraperitoneally according to a similar schedule. Blood is collected at intervals, e.g. 1–2 weeks after each immunization injection. Antisera may be titrated to determine antibody formation with respect to the peptide immunogen, according to standard ELISA or immunoprecipitation methods (Harlow, et al., pp. 423–470, 1988). Example 5 describes a procedure used to produce polyclonal antibodies against helicopeptide I.

D. Binding Affinity

The binding affinity of the antibodies for the helicopeptide, whether the antibodies are monoclonal or polyclonal, can be determined by known methods (e.g., by Scatchard analysis using an immunoprecipitation or ELISA assay (e.g., Campbell, 1991; Segel, 1976).

In the case of polyclonal antibodies, the measured affinity usually represents an average binding affinity constant for a mixture of antibodies present in the antisera which are immunospecific for the selected immunogen. Therefore, polyclonal antibodies may be further purified by affinity chromatography using bound antigen, by methodology known in the art, to enrich for antibodies with high specificity and affinity for the helicopeptide.

As noted above, the antibody of the invention is generally selected to be immunospecific for an epitope contained in helicopeptide I or II above. Preferably, the antibody is characterized by one or more of the following properties, including any possible permutation thereof.

Preferably, the antibody has a binding affinity constant for the helicopeptide of about $1\times10^7$/molar or greater, preferably about $1\times10^8$/molar or greater, and more preferably at least $1\times10^9$/molar. For example, the affinity constant of monoclonal antibody 10B1 for helicopeptide I is about $1\times10^8$/M (Example 4C).

Preferably, the antibody of the invention does not significantly crossreact with intact (triple helical) collagen, particularly collagen Types I through V. The relative crossreactivity of the antibody for any of these collagen species can be determined by standard methods as noted above, using collagens prepared by known methods (e.g., Miller & Rhodes, 1982) or from commercial sources (e.g., Sigma Chem. Co. or Heyl GmbH & Co., Berlin, Germany). For example, monoclonal antibody 10B1 strongly binds helicopeptide I in single-stranded form, but does not crossreact with intact collagen of any of Types I through V. Apparently, the peptide epitope region is constrained to a particular three-dimensional conformation that is not recognized by the antibody's binding site.

Accordingly, in one preferred embodiment, the antibody of the invention is specific for an epitope in helicopeptide I or helicopeptide II in monopeptide form, and does not react to a significant extent with the corresponding epitope sequence in intact, triple helical collagen (e.g., the antibody has a binding affinity for the epitope sequence in triple helical collagen that is at least 10-fold less, and more preferably is at least 100-fold less, than the affinity constant of the antibody for the monopeptide form of helicopeptide I or II, using the protocol in Example 8C).

The antibody may also be selected to have a binding affinity for the corresponding sequence in the $\alpha$1 chain of Type II collagen that is at least 10-fold lower than the antibody's affinity for the corresponding Type I $\alpha$1 helicopeptide (I or II) identified above.

More generally, the antibody should be sufficiently specific for the selected helicopeptide to avoid spurious results due to binding with other components in the sample. Adequate specificity for assaying a particular type of fluid sample can typically be established by spike-recovery studies as illustrated in Examples 9 and 12.

III. Immunoassay Method

The immunoassay method of the invention provides a way to determine the level or helicopeptide I or II in biological fluids.

In a preferred embodiment, the method is useful for measuring or monitoring bone collagen degradation in a mammalian subject, especially humans. The method typically includes the steps of (a) contacting the biological fluid sample with an antibody which is immunospecific for a selected peptide epitope as discussed above, (b) by said contacting, forming an immunocomplex between the antibody and collagen fragments in the sample which contain the selected epitope, (c) measuring the amount of immunocomplex formed, and (d) by said measuring, determining the level of immunologically reactive collagen fragments in the sample. The level determined is compared with a level characteristic of normal subjects, wherein an above-normal level is indicative of an above-normal level of bone collagen resorption, and thus indicates that the subject has a bone resorption disorder.

Where the sample fluid tested is urine, the level of measured collagen fragments may be normalized using a measured level of creatinine or any equivalent thereof, by conventional methods. Urine collection can be in accordance with standard collection protocols, such as 24-hour, first void and second void collection. Preferably, the same mode of sample collection is used for all samples to reduce variation in results.

Blood samples may be converted to serum or plasma by known methods, and may be subjected to further preprocessing if desired. For example, serum can be passed through a spin-filter having a defined molecular weight cutoff (e.g., >20,000 MW) to remove proteins of a selected size from the sample prior to assay.

Conventional methods can be used for any other type of biological fluid sample to be tested.

Sample stability can often be improved by including one or more protease inhibitors to reduce proteolytic degradation of the helicopeptide. Various protease inhibitors are known in the art, including commercially available inhibitor "cocktails" (e.g., from Sigma Chemical Co.), as illustrated in Examples 1 and 12.

The reaction of sample with the antibody reagent may be carried out using any of a variety of immunoassay configurations known in the art, including homogeneous and heterogeneous assay formats. Representative assay formats are described in Examples 8–12.

The detection format may be by any means, including radiotracers (RIA), coupled enzymes, absorbance techniques, fluorescence, chemiluminescence, or EMIT configuration (Gosling, 1990). One preferred reporter is alkaline phosphatase, which can react with a p-nitrophenylphosphate substrate to produce a colored product having a strong absorption peak at 405 nm. An exemplary protocol for preparing a helicopeptide-alkaline phosphatase conjugate is described in Example 3B. It will be appreciated that various other detection modes may be employed, such as a biotin-labeled second antibody in combination with a reporter-labeled streptavidin. A representative methodology for preparing a helicopeptide-streptavidin conjugate is provided in Example 3C.

In an exemplary embodiment of the assay method, a known volume, typically 10–50 µL, of sample is added to an helicopeptide-coated solid support, e.g., the wells in a microtitre plate, and sample addition is followed by addition of a known volume, typically 50–200 µL, of helicopeptide-specific antibody of a known dilution. The mixture on the solid support surface is then incubated, preferably under conditions effective to achieve equilibrium between the antibody binding to sample collagen fragments and surface-bound helicopeptide (e.g., overnight at 2–8° C. or at room temperature for several hours).

After the incubation, the solid support is washed several times to remove antibody not specifically bound to the support, and is then incubated with an enzyme-labeled anti-IgG antibody effective to bind specifically to support-bound antibody. For example, where the helicopeptide-specific antibody is a rabbit polyclonal antibody, the enzyme-labeled antibody can be goat anti-rabbit IgG conjugated with alkaline phosphatase. For a mouse monoclonal antibody reagent, the enzyme-labeled antibody can be a goat anti-mouse IgG derivatized with alkaline phosphatase.

After a short incubation time, the support is again washed to remove non-specifically bound material, and the level of enzyme bound to the support is determined by addition of enzyme substrate, with spectrophotometric determination of converted substrate.

For calibration of the assay, standards containing a range of helicopeptide concentrations are added in duplicate to some of the wells, to generate a standard curve. Up to 40 samples are then added in duplicate to remaining wells, and the wells are then assayed as above.

More generally, the assay format is preferably a competitive, "heterogeneous" immunoassay format in which the reporter label for detection of the immunocomplex is directly attached to either a competitor helicopeptide or to the helicopeptide-specific antibody.

Thus, in one preferred configuration, the helicopeptide-specific antibodies are immobilized on a solid support, and enzyme-labeled helicopeptide is added to compete with collagen fragments in the sample, for binding to the immobilized antibodies. The enzyme label can be alkaline phosphatase or horse-radish peroxidase, for example.

In a second preferred configuration, helicopeptide is immobilized on a solid support to compete with collagen fragments in the sample for binding to non-immobilized enzyme-labeled antibody.

Experiments carried out in support of the invention demonstrate good overall performance of both urine and serum-based assays (e.g., Examples 9 and 12), based on the helicopeptide markers described herein. Assays for biological fluids from other sources can be readily adapted from the methodology discussed herein.

IV. Utility

The present invention provides a method of assessing the level of bone resorption activity in human subjects which is useful in a variety of applications. The method may be used in a screening embodiment or to detect (diagnose) non-invasively the presence of a bone collagen disorder characterized by above-normal bone resorption. Exemplary bone disorders for which the present invention may be useful include osteoporosis, osteoarthritis, rheumatoid arthritis, and conditions related to the progress of benign and malignant tumors of the bone and metastatic cancers that have migrated to bone cells from elsewhere in the body, e.g., from prostate or breast initial tumors. Other conditions include osteomalacial diseases, rickets, abnormal growth in children, renal osteodystrophy, and drug-induced osteopenia. Further, abnormalities in bone metabolism are often side effects of thyroid treatment and thyroid conditions per se, such as primary hyperparathyroidism and thyrotoxicosis as well as Cushing's disease.

Experiments carried out in support of the invention indicate that serum and urine assays based on the helicopeptide markers described herein can detect elevated bone resorption levels in various populations (Examples 10 and 12).

The method may also be used to monitor the progress of an ongoing bone collagen disorder over time, or to monitor a subject's response to therapeutic treatment. A number of anti-resorptive therapies are now under development or are already available for which the invention will be useful. This is illustrated in Example 11 for the known antiresorptive drugs, pamidronate and alendronate, and in Example 13 for pamidronate treatment following thyroid cancer. Similarly, the method may be used in the context of metastatic cancer conditions, to determine whether a primary cancer has spread to the subject's bone tissue, and whether a subject is responding to treatment.

It will be appreciated that the method may also be used with other diagnostic methods, such as radiographic techniques, ultrasound, and assays directed to other indicators of bone resorption status, to provide a fuller picture of the subject's status.

The method and antibodies of the invention are also useful for assessing the effect of selected substances, such as drugs or drug candidates, on the level of expression or secretion of type I collagen and/or fragments thereof by a cell or tissue preparation. Thus, the method can be used with bone-related cells, such as osteoclasts and/or osteoblasts in cell or tissue cultures, for the study of osteogenic substances and the like. The helicopeptide measurements can be conducted on culture supernatants or extracts that are prepared in accordance with conventional methods.

In another embodiment, the invention includes a method of assessing the effect of a selected substance, such as a drug, on helicopeptide levels in a body fluid of an animal model such as rats, mice, cats, dogs, monkeys, etc, using an immunoassay method as described above. The method is useful for identifying and/or characterizing substances and therapies that reduce the level of bone resorption.

Furthermore, the antibody reagent of the invention can also be used in an affinity chromatography matrix, in accordance with standard affinity chromatography methods, for binding and collecting peptides and collagen fragments from biological fluids, e.g., by passing pooled blood or urine through such a matrix.

From the foregoing, it will be appreciated how various objects and features of the invention are met. The invention provides a simple, non-invasive method for measuring certain collagen fragments in biological fluids, which are useful indicators of bone resorption levels. The method also allows the monitoring of changes in disease status during or following therapeutic treatments.

The following examples are intended to illustrate but not limit the invention.

EXAMPLES

Materials and Methods

Cell Lines. Mouse non-secreting myeloma fusion partner P3X63Ag8.653 (ATCC# CRL1580), mouse monocyte-macrophage cell line P388D1 (IL-1) (ATCC# TIB63) and J774A.1 (ATCC# TIB67) were purchased from the American Type Culture Collection (ATCC), Rockville, Md.

Media. Dulbecco's Modified Eagle Media (DMEM) (Cat#320-1995AJ), NCTC-109 (Cat#320-1340AJ), L-glutamine and Gentamicin were purchased from Gibco, Grand Island, N.Y. Fetal clone bovine serum product was obtained from Hyclone Laboratories, Inc., Logan, Utah. Oxaloacetic acid and insulin were purchased from Sigma Chemical company, St. Louis, Mo. S-DMEM was formulated to contain the following: 80% DMEM supplemented with 10% NCTC-109, 10% fetal clone bovine serum product, 1 mM oxaloacetic acid, 2 mM L-glutamine, 50 $\mu$g/mL gentamicin, and 10 $\mu$g/mL insulin, where the percentages indicate final volume percentages in the medium.

Macrophage or Spleen Cell Conditioned Media. Mouse monocyte cell lines P388D1 (IL-1) and J774A.1 were grown in S-DMEM media with a 1:4 division twice a week. The tissue culture supernatants were filtered through a 0.2 $\mu$m filter, and supplemented with 4 mM L-glutamine. These concentrated conditioned media were used as 20% supplement of S-DMEM to raise hybridoma cells. Sigma J774A.1 conditioned medium (Cat# M-8782) was used as 10% supplement of S-DMEM for limiting dilution cloning. Spleen cells were added to S-DMEM for limiting dilution cloning.

Plates. 96, 48, 24, and 6 well flat bottomed tissue culture plates and T-25, T-75, T-225 tissue culture flasks were obtained from Costar, Cambridge, Mass. EIA plates were purchased from Costar (#3590) and Nunc (#AS-72090).

Freezing Media. Sterile DMSO (dimethyl sulfoxide) was purchased from American Type Culture Collection (Rockville, Md.) or from Sigma Chemical Co. Freezing media was formulated to contain 40 mL of S-DMEM, 5 mL of fetal bovine serum, and 5 mL of DMSO.

Mice. Female 5-week-old autoimmune mice MRL/MpJ-lpr were purchased from the Jackson Laboratory, Bar Harbor, Me. Balb/c mice were purchased from Charles River Laboratories, Hollister, Calif.

Buffers. Various buffers used in the protocols below were prepared as follows.

PBS (phosphate-buffered saline): 10 mM or 100 mM sodium phosphate and 150 mM NaCl, pH=7.0.

High detergent wash buffer: 0.005% $NaN_3$ and 0.3% Tween 20 in 10 mM potassium PBS (potassium used in place of sodium).

ELISA wash buffer: 0.005% $NaN_3$ and 0.05% Tween 20 in 10 mM potassium PBS (potassium used in place of sodium).

ELISA assay buffer: 0.05% $NaN_3$, 0.05% Tween 20, and 0.1% BSA (bovine serum albumin) in 100 mM PBS.

ELISA substrate buffer: 0.05% $NaN_3$, 1 M diethanolamine, and 1 mM $MgCl_2$.

PSA (porcine serum albumin) blocking solution: 1 mg/mL pig albumin (Sigma Cat#A-4414) in 10 mM PBS.

Other. Immunoglobulin Isotyping Kit-IsoStrip™ (Cat#1493 027) was purchased from Boehringer Mannhein. Rabbit anti-mouse IgG+A+M (Cat#61-6500) was purchased from Zymed Laboratories, Inc., San Francisco, Calif. Synthetic peptides were obtained from the Beckman Center, Stanford University, Palo Alto, Calif. PNPP (p-nitrophenylphosphate) was obtained from Sigma Chemical Co.

Adjuvant Ribi (MPL+TDM Emulsion) with CWS supplement was purchased from RIBI Immunochem Research, Inc., Hamilton, Mont. BCA protein assay kit (Cat#23225) was purchased from Pierce, Rockford, Ill. PEG 1500 (polyethylene glycol 1500) was purchased from Boehringer Mannheim, Indianapolis, Ind. HAT and HT media were obtained from Sigma Chemical Co., St. Louis, Mo. IFA (Freund's incomplete adjuvant, Cat#77146G) was obtained from Pierce.

Example 1

Isolation and Characterization of Native Helicopeptides

Urine from a patient with severe Paget's disease (alkaline phosphatase>~1000 IU) was combined with a protease inhibitor cocktail consisting of 1 mM phenylmethylsulfonyl fluoride (PMSF), 100 mM N-ethyl maleimide, 50 mM Tris pH 11 in 25% ethanol (20 mL cocktail per 2L sample) and stored at 4° C. until analysis. The urine was concentrated using an Amicon UM-2 filter with a reservoir and automatic cut-off device that permitted concentration of up to 2.5 liters. The concentrate was then dialyzed at 2° C. using Spectrapor™ dialysis membranes with a molecular weight limit of 3500, and then freeze-dried. Portions were then dissolved in 1M $CaCl_2$/50 mM Tris•HCl/0.2% sodium azide/1% protease inhibitor cocktail and chromatographed in the same buffer on Sephadex G-75. Fractions were monitored by $OD_{280}$ and aliquots were hydrolyzed by acid treatment and analyzed for hydroxyproline (Hyp). Tritiated water was used to mark the end of the separation. Results are shown in FIG. 1.

The fractions containing Hyp (fractions 50–70) were collected, pooled, dialyzed to remove buffer constituents, and freeze-dried. The peptides in these fractions were further purified by chromatofocusing (Pharmacia PBE 94 media in 0.9×10 cm column equilibrated to pH 7.4 with 0.025 M imidazole•HCl) for separation according to isoelectric point. A pH 7.5–4.0 polybuffer ampholyte (Pharmacia Polybuffer 74, 110 mL gradient with flow rate of 21 mL/h) was used for chromatofocusing, which was then removed from the eluted peptides by passage through a Sephadex P-10 column (113 cm).

Figure 2:
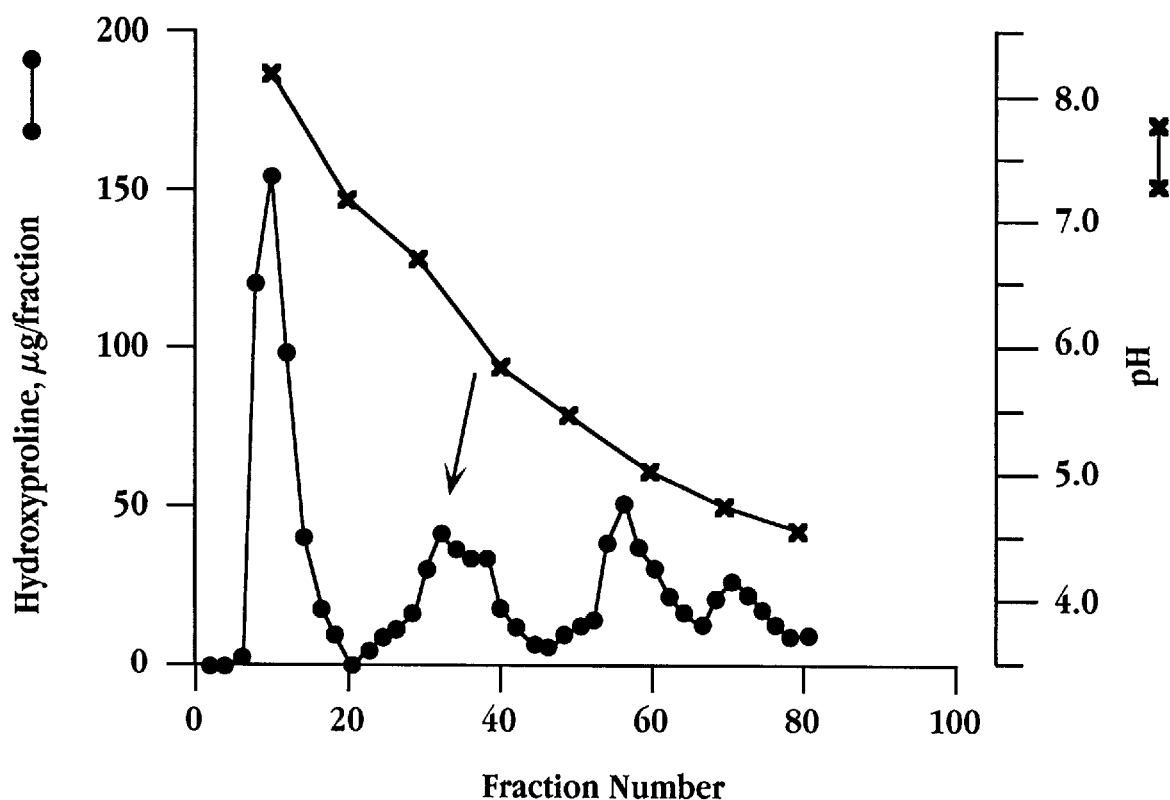
FIG. 2 shows a chromatofocusing separation of pooled Hyp fractions from the preceding chromatographic separation.

The eluted peptides were assayed according to the hydroxyproline assay method of Bergmann & Loxley (1963) using aliquots of up to 100 microliters. Approximately 39% of the hydroxyproline applied eluted immediately in the void volume, followed by elution of three resolved peaks corresponding to pIs of 4.8, 5.3, and 6.2, as shown in FIG. 2.

Figure 3:
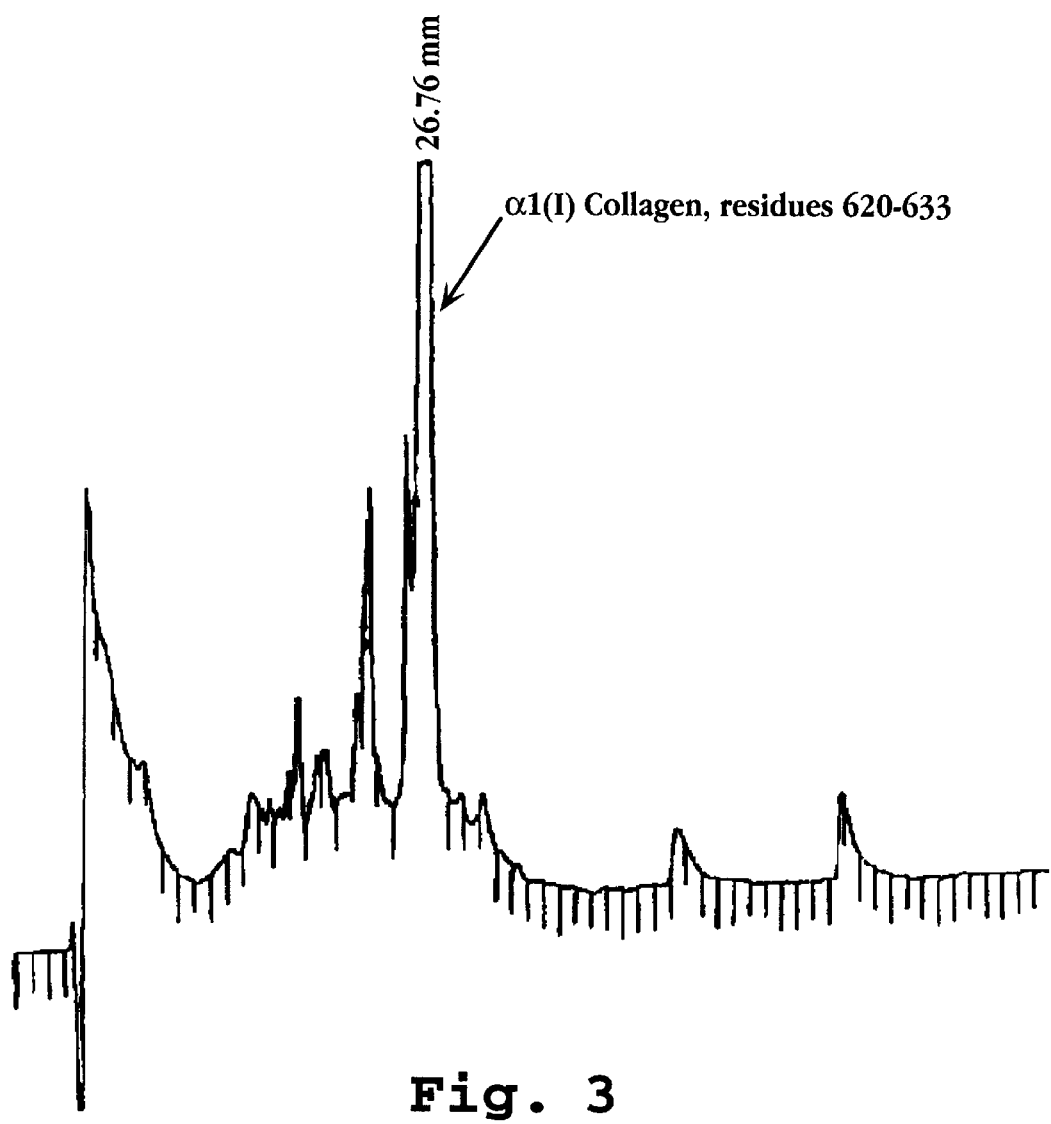
FIG. 3 shows the results of a final HPLC-based separation of pooled Hyp fractions with a pI of ~6.2, indicating the isolation of collagen helicopeptide (I) (Example 2)

Fractions eluting with pI of ~6.2 (indicated by the arrow in FIG. 2) were resolved by HPLC on a C18 Vydac TP201 column using a Beckman HPLC unit, with a combination of two aqueous linear gradients of acetonitrile, according to the method of van der Rest (1982). The acetonitrile gradients employed were (i) heptafluorobutyric acid (4–32% acetonitrile, 90 min) and (ii) 0.009M trifluoroacetic acid (0–32% acetonitrile, 1 h) at a flow rate of 1 mL/min (FIG. 3). Samples corresponding to the peaks were collected and amino acid sequencing was performed on an ABI 470 Amino Acid Sequencer using the Edman degradation procedure. Several peaks were not sequenced due to blocked N-termini. Two fragment sequences were successfully determined:

(1) Ala-Hyp-Gly-Asp-Arg-Gly-Glu-Hyp-Gly-Pro-Hyp-Gly-Pro-Ala (SEQ ID NO:1), and
(2) Gly-Asn-Ser-Gly-Glu-Hyp-Gly-Ala-Hyp (SEQ ID NO:2).

The above peptides correspond to residues 620–633 and 253–261, respectively, of the helical domain of the α1 chain of human Type I collagen.

Example 2

Synthetic Peptides

Synthetic peptides (1) and (2), corresponding to the native sequences SEQ ID NO:1 and 2 (Example 1), respectively, were prepared by standard peptide synthesis methods for use as standards in assays and kits, and for conjugation to alkaline phosphatase. Also for conjugate preparation, synthetic peptides (1) and (2) were modified to include an additional cysteine residue at their N-termini as shown below:

(1a) Cys-Ala-Hyp-Gly-Asp-Arg-Gly-Glu-Hyp-Gly-Pro-Hyp-Gly-Pro-Ala (SEQ ID NO:3), and
(2a) Cys-Gly-Asn-Ser-Gly-Glu-Hyp-Gly-Ala-Hyp (SEQ ID NO:4).

The purity of the resulting synthetic cysteinylated peptides, (1a) and (2a), was confirmed by reverse phase HPLC. Molecular masses were confirmed by mass spectrometry.

Example 3

Helicopeptide Conjugates

A. KLH-Helicopeptide Conjugate

Immunogens for generating antibodies against peptides (1) and (2) were prepared by linking the Cys-helicopeptides from Example 2 to maleimide-modified KLH using sulfo-SMCC (sulfo-N-succinimidyl 4-(N-maleimidomethyl) cyclohexane-1-carboxylate) as follows.

Keyhole limpet hemocyanin (IMJECT, Pierce Chemical, 20 mg, $2.50 \times 10^{-6}$ mmole) was reconstituted in 2.0 mL water, resulting in a 10 mg/mL KLH solution containing 83 mM sodium phosphate, pH 7.2, with 0.9 M NaCl. To this cloudy blue colloidal solution was added a 500-fold molar excess (assuming a molecular weight of 1 million for KLH) of sulfo-SMCC (Pierce Chemical, 6.55 mg in 200 µL DMSO). The resulting solution was then incubated at room temperature for 1.5 to 2 h. The solution was dialyzed for 2 hr at room temperature against 1.8 liter of 100 mM sodium phosphate, pH 6.8, with 150 mM sodium chloride, with one exchange of buffer.

A 1000-fold molar excess of each of cysteinylated peptides (1a) and (2a) was dissolved in 300 µL of 100 mM sodium phosphate, pH 6.8, 150 mM NaCl. To each of the dissolved peptides was added half of the dialyzed KLH-SMCC-containing solution. The resulting mixture was allowed to stand for 2 hr at room temperature. The resulting KLH-conjugates were purified by exhaustive dialysis overnight at 4° C. into PBS, pH 7.1, with one buffer exchange.

Amino acid analysis of the conjugates, KLH-SMCC-N-Cys-helicopeptide (1) and KLH-SMCC-N-Cys-helicopeptide (2) (designated immunogens (3) and (4), respectively), indicated the presence of a substantial amount of hydroxyproline in the conjugates and none in KLH alone, indicating heavy derivatization of carrier KLH with each of the immunogenic peptides. Exact conjugation ratios were not determined due to the heterogeneity of the carrier.

B. Helicopeptide-Alkaline Phosphatase Conjugates

For screening monoclonal antibodies, alkaline phosphate conjugates (conjugates (5) and (6), respectively) were prepared using each of peptides (1a) and (2a) and N-succinimidyl-3-(2-pyridyldithio)propionate (SPDP) as coupling agent.

A 10-fold molar excess of SPDP (Pierce, 6 mg/mL stock solution in DMSO) was added to 3 mg of alkaline phosphatase (Scripps) to form a resulting solution at a concentration of 10 mg/mL protein. After standing for 1 hr at room temperature, the reaction mixture was dialyzed overnight at 4° C. against 1.5 liter of 100 mM sodium phosphate, pH 6.0, with one exchange of buffer.

The dialyzed SPDP-derivatized alkaline phosphatase solution was divided between two reaction containers each containing a 20-fold molar excess of the synthetic helicopeptide (1a) or (1b). After standing for 4 hr at room temperature, the reactions were stopped by addition of N-ethylmaleimide to a final concentration of 75 mM (1 M stock solution in methanol) and allowed to stand for 1 hr.

The resulting conjugates, alkaline phosphatase-SPDP-peptide (5) and alkaline phosphatase-SPDP-peptide (6), were purified by exhaustive dialysis overnight at 4° C. against 1.5 liter of PBS, pH 7.1, with one exchange of buffer.

The alkaline phosphatase conjugates were assayed for alkaline phosphatase activity by observation of the A405 absorbance following treatment with p-nitrophenyl phosphate in diethanolamine substrate buffer.

To determine the corresponding conjugation ratios, the amount of hydroxyproline present in the conjugates was measured by amino acid analysis. The conjugation ratios were the same for both conjugates (six peptides per alkaline phosphatase dimer).

In an alternative approach, alkaline phosphatase conjugates can be prepared as follows: 12.5 mg alkaline phosphatase dialyzed against 10 mM PBS (pH 7) is mixed with 3.2 mg of peptide (1a) or (1b) in 150 μL of 100 mM PBS (pH 7 to 7.5). After the alkaline phosphatase concentration is adjusted to 5 mg/mL with 100 mM PBS, 2.3 mg bis (succinimidyl) suberate (Pierce) is added as a powder, followed by vortexing. The reaction is allowed to proceed for 1.5 h at room temperature. The reaction is quenched with 1 M glycine in 100 mM PBS and dialyzed against 2 liters of 10 mM PBS with five changes over three days.

C. Helicopeptide-Steptavidin Conjugates

Streptavidin conjugates (e.g., for determining the antibody titer) were prepared as follows. A 10-fold molar excess of SPDP (Pierce, 6 mg/mL stock solution in DMSO) was added to 3 mg of streptavidin (Scripps) and the resulting solution was allowed to stand for 1 hr at room temperature. The protein concentration of the resulting reaction mixture was 10 mg/mL. The reaction mixture was dialyzed overnight at 4° C. against 1.5 liter of 100 mM sodium phosphate, pH 6.0, with one exchange of buffer.

The dialyzed SPDP-derivatized streptavidin solution was divided between two reaction containers each containing a 20-fold molar excess of cysteine-containnig helicopeptide (1a) or (2a). After standing for 4 hr at room temperature, the reactions were stopped by addition of N-ethylmaleimide to a final concentration of 75 mM (1 M stock solution in methanol), followed by incubation for 1 hr.

The resulting conjugates, streptavidin-SPDP-N-Cys-helicopeptide (1) and streptavidin-SPDP-N-Cys-helicopeptide (2) (designated conjugates (7) and (8), respectively), were purified by exhaustive dialysis overnight at 4° C. against 1.5 liter of PBS, pH 7.1, with one exchange of buffer. Amino acid analysis indicated conjugation ratios of about 4 peptides per streptavidin tetramer for both conjugate preparations.

Example 4

Monoclonal Antibodies

A. Immunization

Balb/c and MRL/MpJ-1pr mice were immunized with immunogen (3) and (4), respectively, using the protocol below.

TABLE 2A (Balb/c Mice, Immunogen (3))

| Immunization | Days from Fusion | Antigen Injected (μg) | [1]Adjuvant | Inject. Mode |
|---|---|---|---|---|
| 1 | 81 | 100 | Ribi (CWS) | ip[2] |
| 2 | 67 | 100 | Ribi (CWS) | ip |
| 3 | 39 | 100 | Ribi (CWS) | ip |
| 4 | 7 | 200 | — | iv[3], ip |
| 5 | 3 | 200 | — | ip |

[1]Adjuvant and antigen are suspended in Hank's balanced salt solution (HBSS); [2]intraperitoneal; [3]intravenous Best titer results (immunoqen 3): reverse titer ~37,912, forward indirect titer 50,930. (Determined as the reciprocal of the dilution, which has O.D. equivalent to 50% maximum O.D. based upon reverse or forward indirect ELISA).

TABLE 2B (MRL/MpJ-Ipr Mice, Immunogen (4))

| Immunization | Days from Fusion | Antigen Injected (μg) | [1]Adjuvant | Inject. Mode |
|---|---|---|---|---|
| 1 | 81 | 100 | Ribi (CWS) | ip[2] |
| 2 | 67 | 100 | Ribi (CWS) | ip |
| 3 | 39 | 100 | Ribi (CWS) | ip |
| 4 | 7 | 200 | — | ip, iv[3] |

[1]Adjuvant and antigen are suspended in Hank's balanced salt solution (HBSS); [2]intraperitoneal; [3]intravenous Best titer results (immunogen 4): reverse titer 128,477, forward indirect titer, 54,314).

Tail vein bleeds were collected and serum titers were determined around 10 days after the third immunizations using a forward indirect titer determination and a "reverse ELISA" as described below. The best titer mice were boosted intravenously with 200 μg/mL peptide immunogen in HBSS 3 to 7 days before the fusion.

The immunized mice were then sacrificed by $CO_2$ asphyxiation. Each mouse was rinsed with 70% alcohol, placed on its right side on the cutting board, and transferred to a hood. The spleen was transferred to a petri dish containing 5 mL of serum-free DMEM media. The spleen was washed twice in serum-free DMEM media, and then cut into small pieces and homogenized in 7 mL of serum free DMEM in a cell homogenizer.

B. Fusion Protocol

Fusions for immunogen (3) were carried out with approximately $\sim33\times10^6$ myeloma cells and $\sim1\times10^8$ homogenized immune spleen cells; fusions for immunogen (4) were carried out with approximately $\sim66\times10^6$ myeloma cells and $\sim2\times10^8$ homogenized immune spleen cells.

For each fusion, myeloma cells and homogenized immune spleen cells were centrifuged at 1000 rpm for 10 minutes. The pelleted cell mixture was then resuspended in 10 mL serum-free DMEM media (50 mL centrifuge tube) and centrifuged at 1000 rpm for 10 minutes. The supernatant was removed completely, and the tip of the 50 mL centrifuge tube was tapped to loosen the cell pellet. 2 mL of 50% PEG 1500 fusogen was added to the cell pellet dropwise for 90 seconds and mixed gently with a pipette. 2 mL of serum-free DMEM was then added dropwise for 1 minute. 20 mL of S-DMEM was added slowly for 2 minutes, and the cell mixture was allowed to stand for another 2.5 minutes with gentle agitation during the process. The cell suspension was then centrifuged at 1000 rpm for 10 minutes.

After removing the supernatant, the cells were resuspended in 200 mL of HAT in 20% P388D1 or J77S-1 conditioned S-DMEM media. The cell suspension was pipetted into ten 96-well Costar tissue culture plates. The plates were incubated in 7% $CO_2$ at 37° C. to raise the hybridoma cells. Cells were fed on day 3 and day 7 by pipetting out 100 μL/well of the old media, then supplemented with 150 μL/well of HAT (day 3) or HT (day 7) media. The fusion plates were typically ready for screening 7–10 days after the fusion.

In fusion experiments for producing monoclonal antibodies, out of 950 wells for each of immunogens (3) and (4) seeded with cells, all wells appeared to contain viable hybridomas.

C. Screening of Hybridomas

Successful fusion products were then screened for immunoreactivity using the reverse assay format described in Example 8C.

Fusions for immunogen (3): Based upon reverse ELISA, a total of 196 out of 950 wells exhibited good positive results for the fusion (O.D.>1.5), and 32 out of 950 wells showed strong positive results (O.D.>2.0).

Fusions for immunogen (4): Based upon reverse ELISA, a total of 911 out of 950 wells exhibited very strong positive results for the fusion (O.D.>3.0), while 15 out of 950 wells showed good positive results (O.D.>2.0).

Following determination of antibody-producing hybridoma clones, a competitive reverse ELISA protocol was utilized to select clones exhibiting both sensitivity and specificity towards helicopeptide. The competitive reverse ELISA was performed against each of synthetic peptides (1) and (2) and against children's urine as a source of native collagen peptides.

Four clones raised against immunogen (3) exhibited good immunoreactivity against both synthetic peptide (1) and children's urine. One clone, clone 10B1, demonstrated superior immunoreactivity against immunogen (3). Two of the four clones survived the first round of limiting dilution cloning (single cell cloning), one of which was clone 10B1. Based upon its sensitivity and specificity, clone 10B1 was further characterized.

The affinity constant of monoclonal antibody 10B1 was determined to be about $1 \times 10^8$/M, using the protocol described in Example 8C. Clone 10B1 (full name: 10B1-5A6-1C9) was deposited on March 12, 1998 with the ATCC (American Type Culture Collection, 10801 University Blvd, Manassas, Va., 20110-2209) as hybridoma deposit HB-12480 in compliance with the Budapest Treaty.

Example 5

Polyclonal Antibodies

New Zealand white rabbits were immunized with 200 µg/rabbit of immunogen (3) or (4) KLH-SMCC-helicopeptide conjugates from Example 3) with adjuvant Ribi(CWS) every three weeks. Antiserum was collected after the third immunization and 10 days after each subsequent immunization. Titres were analyzed using the following procedure. To each well of a microtitre plate was added 100 µL of 3 µg/mL goat anti-rabbit IgG (Zymed) in 10 mM PBS, followed by overnight incubation at 4° C. The wells were then washed 3 times with 300 µL wash buffer. 100 µL/well of properly diluted rabbit polyclonal serum was added and incubated at room temperature for one hour. After washing the wells three times with 300 µL/well wash buffer, standards (50 µL/well) and urine (1:2 dilution in assay buffer) were added, followed by (50 µL/well) alkaline phosphate conjugates (5) and (6) (Example 3B) in assay buffer. The mixtures were incubated at room temperature for 1 hour, washed 3 times with 300 µL/well wash buffer, and 150 µL/well of 2 mg/mL PNPP substrate solution was added. $OD_{405}$ readings were taken after incubation at room temperature for 1 hour.

Example 6

Preparation of Helicopeptide-Coated Microplates

A. Biotin-PSA

Biotinylation of porcine serum albumin (PSA) was carried out by adding 10 mg of biotin-X-2,4-dinitrophenol-X-L-lysine, succinimidyl ester (Molecular Probes, Eugene, Oreg.) in 400 microliters of dimethylformamide (DMF) to a 15 mL solution of PBS containing 150 mg of albumin. The mixture was allowed to react for two hours at room temperature, followed by G-25 column chromatography.

B. Coating with Helicopeptide-Streptavidin Conjugate

Conjugates (7) and (8) from Example 3C are optionally purified by gel filtration using Sephacryl S-300 HR (1.6×98 cm), eluting with 50 mM PBS pH 7.5 containing 0.05% Tween 20 at 0.33 mL/min.

Each of the wells in a 96-well ELISA plate was coated with conjugate (7) or (8) as follows. To each well was added 150 microliters of biotin-PSA solution at 3.8 µg/mL in PBS, followed by an overnight incubation at 2–8° C. The microplates were washed with PBS containing 0.3% "TWEEN"-20 and blocked by addition of 200 microliters of albumin at 1 mg/mL, followed by an overnight incubation at room temperature. The microplates were then twice washed with PBS containing 0.05% "TWEEN"-20.

To each biotin-PSA coated well was added 150 microliters of a solution containing conjugate (7) or (8) at 100 ng/mL in PBS. After a one hour incubation at room temperature, the plates were twice washed with PBS containing 0.05% "TWEEN"-20, followed by incubation with 200 µL/well of 10% sucrose in 100 mM PBS for 2 hours, to improve the stability of the support. After aspiration of the wells, residual liquid was then removed from the microplate by drying overnight in a convection oven at 37° C.

Example 7

IgG Antibody-Alkaline Phosphatase Conjugate

Ten equivalents of N-succinimidyl 3-(2-pyridyldithio) propionate (SPDP) (Pierce Chemical; 0.22 mg, $6.92 \times 10^{-4}$ mmole) at 4 mg/mL in anhydrous ethanol was immediately added dropwise to alkaline phosphatase (Biozyme; 9.7 mg, $6.92 \times 10^{-5}$ mmole) at 12.2 mg/mL in 0.05 M sodium phosphate buffer pH 7.5 containing 1 mM EDTA and deoxygenated with argon gas. The mixture was then allowed to stand at room temperature for 2.5 h. The resulting alkaline phosphatase-pyridyldithiopropionate product was purified by dialysis against 0.1 M sodium phosphate buffer pH 6 containing 1 mM EDTA and deoxygenated with argon gas.

Conversion to the corresponding thiol was carried out by exposing the alkaline phosphatase-pyridyldithiopropionate product to excess dithiothreitol (Molecular Probes; 2.3 mg, 0.02 mmole) at 5 mM for 30 min. An aliquot was measured by $A_{280}$ and $A_{344}$ and determined to contain 4.8 thiol groups per enzyme. The enzymethiol was purified by gel filtration on Sephadex G-25.

Ten moles of sulfosuccimidyl 4-(N-maleimidomethyl cyclohexane-1-carboxylate (Pierce Chemical; 0.087 mg, $2.00 \times 10^{-4}$ mmole) at 2 mg/mL in anhydrous methanol was immediately added dropwise to protein A-purified peptide-specific IgG antibody ($2.00 \times 10^{-5}$ mmole) at 6.0 mg/mL in 0.0.5 M sodium phosphate buffer pH 7.5 containing 1 mM EDTA and deoxygenated with argon gas, and this was allowed to stand at room temperature for 2.25 h. The resulting IgG-maleimide was purified by dialysis against 0.1 M sodium phosphate buffer pH 6 containing 1 mM EDTA and deoxygenated with argon gas.

The IgG-maleimide was then added directly to 2.6 moles of the alkaline phosphatase-thiol, sealed under argon gas, and allowed to stand at 4° C. for 24 h. Residual thiol groups were then capped with 50 mM N-ethyl maleimide by reacting >24 h at 4° C.

The resulting IgG-alkaline phosphatase conjugate was then purified to remove residual unreacted IgG, enzyme, and NEM by gel filtration through Sephacryl S-300HR (1.6×98 cm), eluting with 50 mM PBS pH 7.5 containing 0.05% Tween 20. The IgG-enzyme containing fractions, relative to non-conjugated material, were first determined by absorbance at $A_{280}$, combined with analysis of diluted aliquots on microtiter plates.

First, the activity of the enzyme was tested by observing the $A_{405}$ absorbance after treatment with p-nitrophenyl phosphate in diethanolamine substrate buffer. Second, the conjugate was identified by binding to a rabbit anti-mouse antibody coated microtiter plate (at 3 µg/mL), washing, and detecting with p-nitrophenyl phosphate in diethanolamine substrate buffer.

Lastly, the conjugate was assayed by binding to a helicopeptide coated plate (PSA-biotin at 3.75 µg/mL overnight at 4° C., blocking the plate with 1 mg/mL PSA solution, followed by streptavidin-peptide conjugate (Example 3C) at 3.8 µg/mL overnight at 4° C., and then detecting any bound IgG-enzyme with 2 mg/mL p-nitrophenyl phosphate in diethanolamine. Fractions are pooled based on these results to obtain only fractions containing IgG-AP conjugate.

Example 8

Illustrative Assay Configurations

A. Forward Direct Format

The following steps are carried out to prepare various assay configurations:

(1) ELISA plates are coated with 150 µL/well, 3.75 µg/mL biotin-PSA at 4° C. for overnight.

(2) The plates are soaked with 250 µL/well high detergent wash for 2 hours.

(3) The plates are blocked with 250 µL/well, 1 mg/mL PSA at 4° C. for overnight.

(4) The plates are washed two times with wash buffer.

(5) Streptavidin-labeled conjugate (7) or (8) (~2 µg/mL) is added to the plates, 150 µL/well, at 4° C. overnight.

(6) The plates are washed three times with wash buffer.

(7) 100 µL/well of antibody-AP conjugate (1:1000 dilution, ~84 ng/mL) in assay buffer and with 50 µL/well standards or samples are added on the plate. The plate is incubated for 1 hour or longer.

(8) The plates are washed three times with 300 µL/well wash buffer.

(9) 150 µL/well of 2 mg/mL PNPP in substrate buffer is added to the plates and incubated at room temperature for 60 minutes or longer. The color development is stopped with 3 N NaOH. The absorbance is measured at 405 nm.

B. Forward Indirect Format

The procedure in part A above is modified as follows. The following modifications are made in place of steps (7) and (8) :

(7) 100 µL/well of helicopeptide-specific antibody (~10 to 50 ng/mL) in assay buffer, and with 50 µL/well of helicopeptide standard or sample, are added to the plate. The plate is incubated for 1 hour or longer.

(8) The plates are washed three times with 300 µL/well of wash buffer.

(8.5) 150 µL/well of Pierce goat anti-mouse IgG+M(H+L) -alkaline phosphatase conjugate (1:1,000 dilution in assay buffer) is added to the ELISA plate and incubated at room temperature for one hour.

C. Reverse Format (1) A Costar or Nunc ELISA plate is coated with 150 µL/well of 3 or 4 µg/mL Zymed rabbit anti-mouse IgG+A+M (H+L) in 10 mM PBS at room temperature for 1–24 hours.

(2) The plate is incubated with a 300 µL/well high detergent wash at room temperature for 2 hours, and then washed two more times.

(3) Antibodies (e.g., anti-helicopeptide (I) or anti-helicopeptide (II) monoclonal antibodies) from cell culture supernatants, mouse sera, or as purified antibodies, are added in assay buffer (e.g., 180 µL/well of antibody 10B1 at 50 ng/mL) and incubated at room temperature for 16–24 hours.

(4) The plates are washed one to three times with 300 µL/well wash buffer, followed by 250 µL/well of a solution 10% sucrose, 1% BSA and 0.05% $NaN_3$ in 100 mM PBS at room temperature for at least one hour.

(5) After the wash, the plate is incubated with 250 µL/well 15% sucrose in 100 mM PBS for 30 minutes to 1 hour. After removing the sucrose solution, the plate is dried overnight at 37° C. in an incubator and then stored with a dessicant.

(6) Add 20 µL biological fluid sample or standard into each well.

(7) Add 150 µL of appropriate dilution of peptide-alkaline phosphatase conjugate in buffer containing 0.5 M $K_2SO_4$, 4 mM $MgCl_2$, and 0.4 mM $ZnCl_2$. Incubate for 3 hours at room temperature (also acceptable: 1 hour to overnight, room temperature or 4° C.).

(8) Wash three times with wash buffer.

(9) Add 100–150 µL/well of 2 mg/mL PNPP in substrate buffer to the plates and incubate at room temperature for 30–60 minutes, after which color development is stopped with 1 N NaOH. The absorbance is measured at 405 nm, followed by four-parameter curve fitting.

Example 9

Urine Peptide Assay

The reverse format procedure in Example 8C was used to characterize the analytical performance of an exemplary assay.

To an anti-helicopeptide (I) monoclonal antibody-coated microtiter plate was added 20 µL of calibrator or urine sample (duplicate), followed by addition of 150 µL of peptide-alkaline phosphatase conjugate in 0.5 M $K_2SO_4$ containing 4 mM $MgCl_2$ and 0.4 mM $ZnCl_2$. The plate was incubated for three hours at room temperature and then washed three times with wash buffer. Colorimetric detection was carried out by addition of 150 µL of PNPP substrate solution (2 mg/mL), followed by incubation for one hour at room temperature. A volume of 100 µL 1N NaOH stop solution was then added to each well. The absorbance was then measured at 405 nm.

Precision. The ELISA exhibited good analytical performance with an intra-assay coefficient variation (CV) of 4–7% and an inter-assay coefficient variation (CV) of 5–7%. These results are summariazed in Table 3 below.

Linearity. The mean linearity was determined as the average of 8 samples measured neat or diluted 1:2, 1:4, 1:8, and 1:16 with assay buffer. The mean urine linearity recovery was 104±8% over the dilutions, where % linearity recovery=(observed value/expected value)×100.

Spike Recovery. Mean spike recovery was determined by spiking different amounts of synthetic peptide (I) (100 ng/mL, 300 ng/mL, and 1000 ng/mL) into 9 urine samples. Mean spike recovery was 99±4%.

Figure 4:
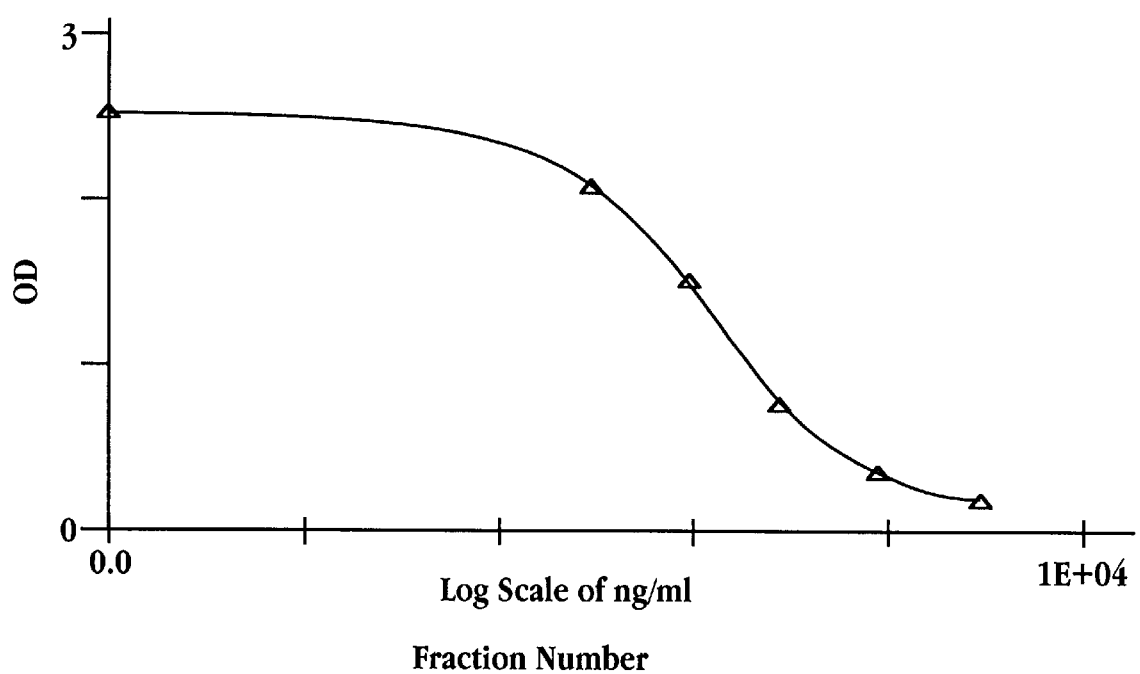
FIG. 4 shows a standard curve for an immunoassay of the present invention.

A standard curve for the urine type I collagen assay based upon detection of helicopeptide (I) is shown in FIG. 4.

TABLE 3

Analytical Performance of Assay

| Sample | Urine Peptide ng/mL* | Intra-Assay CV* | Urine Peptide ng/mL** | Inter-Assay** |
|---|---|---|---|---|
| 1 | 117 | 7% | 127 | 7% |
| 2 | 344 | 5% | 356 | 7% |
| 3 | 708 | 4% | 729 | 5% |

*n = 26–28 reps/run
**n = 2 reps/run, 10 runs, 2 days

The results in Table 3 illustrate good overall analytical performance of a representative reverse ELISA containing anti-helicopeptide monoclonal antibodies for detecting the helicopeptide markers of the present invention.

Example 10

Detecting Bone Resorption in Various Populations

Utilizing the ELISA described in Example 9, assays were performed on samples of urine from the following populations: (i) 73 healthy premenopausal women, ages 25–44; (ii) 20 healthy men, ages 25–44; (iii) 30 patients with Paget's disease, and (iv) 47 osteoporotic women.

Figure 5:
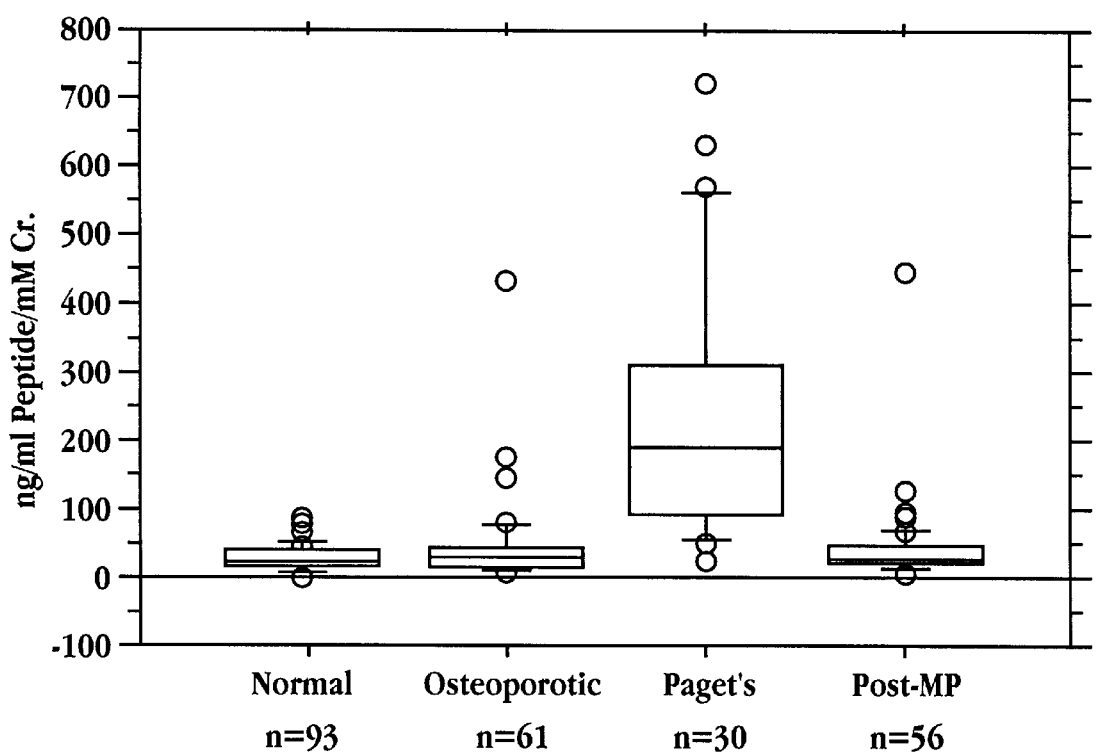
FIG. 5 shows urinary levels of a Type I collagen helicopeptide as measured in normal, osteoporotic, Pagetic, and post-menopausal subjects using an immunoassay in accordance with the present invention.

Based on the results of the assay, the mean urinary level of peptide/$\alpha 1(I)^{620-633}$ (I) in normal populations (i) and (ii) was 30.0±17.9 ng/nmol creatinine. The mean level of marker (I) in patients with Paget's disease was 241.7, with 27 out of 30 of the samples containing >60.0 ng/nmol creatinine (vs. normal P <0.0001). The mean level of marker (I) in osteoporotic women (population (iv)) was 40.4±33.5 ng/nmol creatinine. These results are presented graphically in FIG. 5 and in Table 4 below.

TABLE 4

Population Comparisons

| Population | Urinary Peptide (SEQ ID NO:1) | | |
|---|---|---|---|
| | P Value | T-score | Elevation |
| Normal vs. Post-MP | 0.0585 | 0.71 | 42% |
| Normal vs. Osteoporotic | 0.041 | 0.76 | 45% |
| Normal vs. Paget's | <0.0001 | 12 | 703% | p value: unpaired student t-test; T-Score: test mean-reference population mean/(reference population SD); % elevation: [(test mean-reference population mean) –1] × 100%

Example 11

Monitoring Therapeutic Treatment

The ELISA described in Example 10 was employed to monitor changes in the status of bone degradation in response to therapeutic treatment with pamidronate and alendronate.

Pamidronate Therapy. The study was carried out on a total of 24 subjects. The duration of the study was 26 weeks.

14 osteoporotic female patients were placed on a continuous treatment regimen of 150 mg oral pamidronate disodium (ADP) administered daily over a period of 26 weeks. 10 additional subjects received a weekly maintenance regimen of 150 mg pamidronate daily for a 4-week loading dose period, followed by a weekly maintenance dose of oral pamidronate (150 mg taken one day a week), accompanied by a matching pamidronate placebo taken 6 days a week for the remaining 22 week course of the study.

Urine samples (24 hour pooled samples) were collected prior to treatment to establish a baseline, and at 6-months following the course of treatment.

Alendronate Therapy. 11 female patients having low bone mass (not necessarily osteoporetic) were treated daily with 10 mg oral alendronate. Second morning void urine samples for analysis were collected at baseline (prior to treatment), one month (2 patients), 3 months (6 patients), and 6 months (3 patients) after treatment was started.

Results. The results are summarized below in Tables 5–7. In 24 osteoporotic patients treated with pamidronate (Table 6), excretion of urinary peptide/$\alpha 1(I)^{620-633}$ decreased by a mean of 69%, and decreased by greater than 40% in 22 out of the 24 patients. Similarly, in 11 osteoporotic patients treated with alendronate (Table 7), excretion of urinary peptide/$\alpha 1(I)^{620-633}$ decreased by a mean of 80%, and decreased by greater than 60% in 9 out of 11 patients.

These results show that measurement of the urinary excretion of peptide/$\alpha 1(I)^{620-633}$ by ELISA provides (i) a good marker of bone resorption, and (ii) a sensitive indicator for monitoring the efficacy of various antiresorptive therapies.

TABLE 5

Mean, SD, and % CV of 72 Healthy Premenopausal Women

| Assay | Urine Peptide |
|---|---|
| Unit | ng/mL Peptide/mM Cr. |
| Mean | 30.42 |
| SD | 18.08 |
| CV, % | 59 |

TABLE 6

Mean Response of 24 Patients After Pamidronate Therapy

| Assay | Urine Peptide (I) |
|---|---|
| Mean Drop | 69% |
| SD | 24% |

TABLE 7

Mean Response of 11 Patients After Alendonate Therapy

| Assay | Urine Peptide |
|---|---|
| Mean Drop | 80% |
| SD | 28% |

Example 12

Serum Assays

For the following two protocols, stability of serum samples was improved by including a protease inhibitor cocktail (Sigma #P8340) at a concentration of 2% (v:v).

A. Protocol 1

To a microtiter plate coated with anti-helicopeptide (I) monoclonal antibody (10B1) was added 50 µL (or 100 µL) of calibration standard or serum sample, followed by 100 µL (or 50 µL) of collagen peptide-alkaline phosphatase conjugate. The plate was incubated at 4° C. for 3 hours (or overnight) and washed three times with wash buffer.

Colorimetric detection was carried out by addition of 150 µL of PNPP substrate solution (2 mg/mL), followed by incubation for one hour at room temperature. A volume of 100 μL 1N NaOH stop solution was then added to each well. The absorbance was then measured at 405 nm.

B. Protocol 2

To a plate coated with monoclonal antibody 10B1 prepared as described in Examples 8C (steps 1 to 5) was added 50 μL/well of pH 2-treated total (non-specific) rabbit serum antibodies in 2% DMSO assay buffer (to reduce non-specific binding), followed by 50 μL of serum sample or standard. Peptide-alkaline phosphatase conjugate (50 μL) in 0.5 M $K_2SO_4$ containing 4 mM $MgCl_2$ and 0.4 mM $ZnCl_2$ was then added, and the plate was incubated at 4° C. for 3 hours to overnight.

Following incubation, the plate was washed three times with 300 μL/well wash buffer. Colorimetric detection was carried out by addition of 150 μL of PNPP substrate solution (2 mg/mL), followed by incubation for one hour at room temperature. Stop solution (100 μL 1N NaOH) was added to each well, and the absorbance was measured at 405 nm.

C. Results

Precision. The serum-based ELISA exhibited high precision as indicated by the following parameters.

1. Intra-assay coefficient variation (CV), (n=26–28 replicates): 2.8% (at 25 ng/mL); 7.74% (at 13.4 ng/mL); and 8.4% (at 8.14 ng/mL).
2. Inter-assay coefficient variation (CV) (n=2 replicates per run, 7 runs, 2 days): 8% (at 17.5 ng/mL); and 11% (at 76 ng/mL).

Linearity. The mean linearity was determined as the average of 5 serum samples measured neat or diluted 1:2, 1:4, and 1:8 with assay buffer. The mean serum dilution recovery was 112±6% over the dilutions.

Spike Recovery. Mean spike recovery was determined by spiking 15 serum samples with 10% by volume of synthetic peptide (I) at various concentrations (10 ng/mL, 30 ng/mL, and 100 ng/mL). Mean spike recovery was 93±3%.

Clinical Performance of Serum Assay for Detecting Bone Resorption in Various Populations. The above-described assays were used to determine the amount of helicopeptide (I) in serum samples from various populations, and to evaluate the efficacy of the assay in discriminating between normal and disease patients.

Serum samples from the following populations were collected: (i) 24 healthy premenopausal females; (ii) 35 normal males; (iii) 29 patients with Paget's disease.

Based on the results of the assay, the mean serum level of peptide/$\alpha 1(I)^{620-633}$ in normal premenopausal females was 17.8±4.6 ng/mL, and 16.7±7.2 ng/mL for normal males. Also, 62% (18/29) of the Paget's patients had serum peptide levels that exceeded the normal mean in females by at least 2-fold.

These results show that the helicopeptides of the present invention (i) are effective markers for determining the status of bone resorptive processes, (ii) can be used to detect specific bone-related diseases, and (iii) can be employed in a variety of assay types and configurations using various biological fluid samples such as urine and serum.

Example 13

Pamidronate Treatment with Thyroid Cancer 42 thyroid cancer patients on suppressive doses of thyroxin were administered 30 mg of pamidronate by infusion, or a placebo. Serum and urine samples were collected at baseline (before drug administration), and 1, 2, 3 and 12 months following the start of drug administration, and the level of helicopeptide I was determined using the assay protocols of Examples 9 and 12B. A minimum significant change (MSC) was defined as 2 times long-term intraindividual variability (based on levels at baseline, 1, 2, and 3 months on placebo) Results are shown in the table below:

TABLE 8

|  | Max decrease (%) | MSC (%) (=2 × % CV) | % samples exceeding MSC |
| --- | --- | --- | --- |
| urinary peptide | 72 (n = 21) | 40 (n = 21) | 86 (18/21) |
| serum peptide | 17 (n = 11) | 34 (n = 15) | 27 (3/11) |

Although the invention has been described with respect to specific embodiments and examples, it will be appreciated that various changes and modifications may be made without departing from the invention.

It is claimed:

1. A method for determining the level of Type I collagen fragments in a fluid sample comprising contacting a fluid sample with an antibody which is immunospecific for an epitope contained in the following peptide sequence:

(1) Ala-Hyp-Gly-Asp-Arg-Gly-Glu-Hyp-Gly-Pro-Hyp-Gly-Pro-Ala (SEQ ID NO:1) or under conditions effective to form a complex between said antibody and polypeptide fragments containing said epitope in the sample, determining the level of complex formed, and from the determined level of complex, determining the level of polypeptide fragments that contain the epitope in the sample.

2. The method of claim 1, wherein said antibody is a polyclonal antibody.

3. The method of claim 1, wherein said antibody is a monoclonal antibody.

4. The method of claim 1, wherein the biological fluid sample is a urine sample.

5. The method of claim 1, wherein the biological fluid sample is a blood sample.

6. The method of claim 1, wherein the biological fluid sample is a cell culture supernatant or tissue culture supernatant.

7. The method of claim 1, for use in measuring a level of bone collagen resorption in a mammalian subject, wherein a determined fragment level that is above a fragment level characteristic of normal subjects is an indication that the subject has a bone resorption disorder.

8. The method of claim 7, for use in screening for the presence of a bone resorption condition selected from osteoporosis, osteoarthritis, hyperparathyroidism, rheumatoid arthritis, and a metastatic bone cancer condition.

9. The method of claim 7, for use in monitoring the level of bone collagen resorption in a subject in response to a therapeutic treatment.

10. The method of claim 7, wherein the biological fluid sample is a urine sample.

11. The method of claim 7, wherein the biological fluid sample is a blood sample.

12. An antibody which is immunospecific for an epitope contained in the following peptide sequence:

(1) Ala-Hyp-Gly-Asp-Arg-Gly-Glu-Hyp-Gly-Pro-Hyp-Gly-Pro-Ala (SEQ ID NO:1) or.

13. The antibody of claim 12, which is a monoclonal antibody.

14. The antibody of claim 12, which is a polyclonal antibody.

15. The antibody of claim 12, wherein the antibody has a binding affinity for said epitope of at least $1 \times 10^7$/molar.

16. A test kit for measuring the level of collagen fragments in a biological fluid sample, said kit comprising an antibody which is immunospecific for the epitope defined in claim 12, and a standard containing the epitope for which the antibody is immunospecific.

17. An isolated peptide consisting of an amino acid sequence corresponding to SEQ ID NO:1.

18. An antigen comprising a peptide of claim 17 linked to a carrier.

19. An antigen of claim 18, where the carrier is effective to facilitate an immunological response against the peptide.

20. An immortalized cell line that produces an antibody in accordance with claim 12.

* * * * *

UNITED STATES PATENT AND TRADEMARK OFFICE
CERTIFICATE OF CORRECTION

PATENT NO. : 5,972,623
DATED : October 26, 1999
INVENTOR(S) : Krane et al.

It is certified that error appears in the above-indentified patent and that said Letters Patent is hereby corrected as shown below:

ON TITLE PAGE

Item [73] Assignee: add General Hospital Corporation, Boston, Massachusetts.

Signed and Sealed this

Seventeenth Day of April, 2001

Attest:

NICHOLAS P. GODICI

Attesting Officer

Acting Director of the United States Patent and Trademark Office